United States Patent [19]

Kober et al.

[11] Patent Number: 5,110,829
[45] Date of Patent: May 5, 1992

[54] 2,2'-THIENYLBENZOTHIOPHENES, THEIR PREPARATION AND THEIR USE FOR CONTROLLING PESTS

[75] Inventors: Reiner Kober, Fussgoenheim; Hans Theobald, Limburgerhof; Uwe Kardorff, Mannheim; Christoph Kuenast, Otterstadt; Peter Hofmeister, Neustadt; Rainer Seele, Fussgoenheim; Gerhard Wagenblast, Weisenheim, all of Fed. Rep. of Germany

[73] Assignee: BASF Aktiengesellschaft, Ludwigshafen, Fed. Rep. of Germany

[21] Appl. No.: 737,738

[22] Filed: Jul. 30, 1991

[30] Foreign Application Priority Data

Jul. 31, 1990 [DE] Fed. Rep. of Germany ........ 4024206

[51] Int. Cl.$^5$ .................... A61K 31/38; C07D 333/64
[52] U.S. Cl. ...................... 514/443; 549/49; 549/51; 549/52; 549/56; 549/58
[58] Field of Search ............ 549/49, 51, 52, 54, 549/56, 58; 514/443

[56] References Cited

U.S. PATENT DOCUMENTS 3,050,442 8/1962 Bijloo et al. .................. 549/59
3,706,767 12/1972 Kaltenbronn ................. 260/330.5

FOREIGN PATENT DOCUMENTS 0054233 6/1982 European Pat. Off. .
0353667 2/1990 European Pat. Off. ........ 549/59
WO86/05949 10/1986 PCT Int'l Appl. ............ 549/59

OTHER PUBLICATIONS

K. J. Brown et al., *Tetrahedron Letters*, "A New Approach to the Synthesis of 2-Substituted Benzothiophenes and Their Hetero-Analogues", No. 46, pp. 4069–4072 (1974).

F. J. Gommers et al., *Photochem. Photobiol.*, "Dithiophenes as Singlet Oxygen Sensitizers", 35, pp. 615–619 (1982).

T. Murthy et al., *J. Sci Industr. Res.*, "Thiophenes and Thiapyrans", 19B, pp. 395–401 (1960).

*Primary Examiner*—Richard L. Raymond
*Assistant Examiner*—Mark W. Russell
*Attorney, Agent, or Firm*—Keil & Weinkauf

[57] ABSTRACT 2,2'-Thienylbenzothiophenes of the general formula I

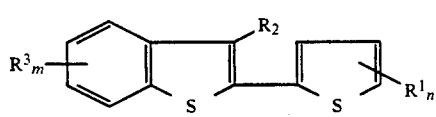

where $R^1$ and $R^3$ independently of one another are each halogen, alkyl, haloalkyl, alkoxy or haloalkoxy, $R^2$ is hydrogen, halogen, alkyl, haloalkyl, alkoxy or haloalkoxy, n is 0, 1 or 2, and the radicals may be different when n is 2, and m is 0, 1, 2, 3 or 4, and the radicals may be different when m is 2, 3 or 4, processes for their preparation, pesticides containing them and the use thereof.

5 Claims, No Drawings

2,2'-THIENYLBENZOTHIOPHENES, THEIR PREPARATION AND THEIR USE FOR CONTROLLING PESTS

The present invention relates to 2,2'-thienylbenzothiophenes of the general formula I

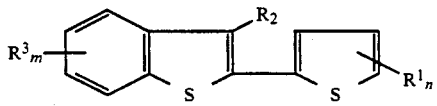

where $R^1$ and $R^3$ independently of one another are each halogen, $C_1$-$C_8$-alkyl, $C_1$-$C_6$-haloalkyl, $C_1$-$C_6$-alkoxy or $C_1$-$C_6$-haloalkoxy, $R^2$ is hydrogen, halogen, $C_1$-$C_8$-alkyl, $C_1$-$C_6$-haloalkyl, $C_1$-$C_6$-alkoxy or $C_1$-$C_6$-haloalkoxy, n is 0, 1 or 2, and the radicals may be different when n is 2, m is 0, 1, 2, 3 or 4, and the radicals may be different when m is 2, 3 or 4, and n and m are not simultaneously 0 when $R^2$ is hydrogen.

The present invention furthermore relates to processes for the preparation of these compounds, agents containing them and the use of compounds of the general formula IA

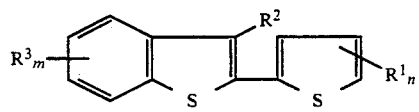

where $R^1$ and $R^3$ independently of one another are each halogen, $C_1$-$C_8$-alkyl, $C_1$-$C_6$-haloalkyl, $C_1$-$C_6$-alkoxy or $C_1$-$C_6$-haloalkoxy, $R^2$ is hydrogen, halogen, $C_1$-$C_8$-alkyl, $C_1$-$C_6$-haloalkyl, $C_1$-$C_6$-alkoxy or $C_1$-$C_6$-haloalkoxy, n is 0, 1 or 2, and the radicals may be different when n is 2, m is 0, 1, 2, 3 or 4, and the radicals may be different when m is 2, 3 or 4, for controlling pests.

It is known that certain bis- and terthiophene compounds have nematocidal activity (U.S. Pat. No. A 3,050,442; WO-A 85/05949). Compounds of this type are furthermore known to have herbicidal activity (EP-A 353 667). In addition to the herbicidal properties, which are undesirable in pesticides, the known bis- and terthiophene compounds lead to undesirable irritation during use when they come into contact with the skin (Photochem Photobiol., 35 (1982), 615 et seq.).

The preparation of 2,2'-thienylbenzothiophene has also been described (Tetrahedron Lett. 46 (1974), 4069; J. Sci. Ind. Res., Sect. B 19 (1960), 395 and 400). However, it is questionable as to whether the product described in this literature is in fact 2,2'-thienylbenzothiophene, since the melting point described is more than 20° C. higher than the melting point of the 2,2'thienylbenzothiophene which is obtained in connection with the present invention and whose structure has been confirmed on the basis of preparation methods with unambiguous coupling reactions (Wittig synthesis starting from thiophene-2-carbonyl chloride and the triphenylphosphonium salt of 2-mercaptobenzyl bromide and subsequent cyclization) and physical investigations ($^1$H- and $^{13}$C-NMR data, IR data and combustion analysis). Experiments to prepare 2,2'-thienylbenzothiophene by the processes disclosed in the literature have been unsuccessful to date.

It is an object of the present invention to provide novel insecticidal compounds which do not have the disadvantages described above with regard to the herbicidal action and the danger to the user.

We have found that this object is achieved by the compounds I defined at the outset.

We have also found processes for the preparation of the compounds I and the use of the compounds IA for controlling pests.

The compounds I are obtained, for example, by coupling a 2-halobenzothiophene of the general formula II with a thienyl-Grignard compound of the general formula III in a conventional manner (Heterocycles 24 (10) (1986), 2901 et seq.) in an inert organic solvent in the presence of a catalyst.

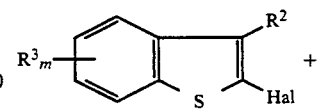

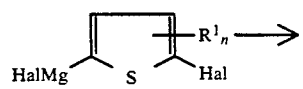

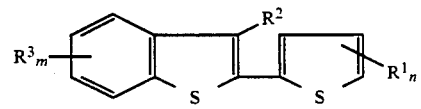

In formulae II and III, the radicals Hal independently of one another are each halogen, such as fluorine, chlorine, bromine or iodine, in particular chlorine or bromine.

Suitable solvents for this reaction are organic solvents, such as ethers, in particular diethyl ether, diisobutyl ether, tert-butyl methyl ether, tetrahydrofuran and dioxane, and aliphatic and aromatic hydrocarbons and halohydrocarbons, in particular n-pentane, n-hexane, cyclohexane, toluene and chlorobenzene, and corresponding mixtures.

A particularly suitable catalyst is Ni(DPPP)Cl$_2$ (DPPP=1,3-bis-(diphenylphosphino)-propane). The catalyst is used in general in not more than 5.0, preferably not more than 2.0, in particular from 1.1 to 1.35, mol %, based on the educt II or III.

The reaction usually takes place at a sufficient rate at above 0° C. Since the reaction is generally exothermic, it may be advantageous to provide a source of cooling.

As a rule, the reaction is carried out at from 0° to 50° C., preferably from 10° to 40° C., in particular from 20° to 30° C.

In general, the compounds III and the compounds II are reacted with one another in equimolar amounts. It may be advantageous for the yield to use the benzothiophene in excess or in less than the stoichiometric amount, based on the Grignard reagent. For economic reasons, the educt used in excess is usually that which is easier to prepare or cheaper to obtain.

The 2-halobenzothiophene derivatives of the general formula II which are required for the reaction are disclosed in the general literature or can be prepared by the processes described there (cf. Adv. in Het. Chem. 11 (1970), 370 et seq.).

The thienyl-Grignard compounds III required for the preparation of the compounds I are known from the literature cited at the outset or obtainable by the processes described there (cf. EP-A 353 667; Heterocycles 24 (10) (1986), 2902 et seq.).

In view of the intended use of the compounds IA, suitable substituents are the following radicals:

$R^1$ and $R^3$ independently of one another are each halogen, such as fluorine, chlorine, bromine or iodine, in particular chlorine or bromine;

$C_1$–$C_8$-alkyl, in particular branched or straight-chain $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular branched or straight-chain $C_1$–$C_4$-alkyl, such as methyl, ethyl, propyl, 1-methylethyl, butyl, 1-methylpropyl, 2-methylpropyl or 1,1-dimethylethyl;

$C_1$–$C_6$-haloalkyl, preferably $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl,2-chloro-2,2-difluoroethyl,2,2-dichloro-2-fluoroethyl, 2,2,2-trichloroethyl and pentafluoroethyl, in particular trifluoromethyl;

$C_1$–$C_6$–such as methoxy, ethoxy, propoxy, 1-methylethoxy, butoxy, 1-methylpropoxy, 2-methylpropoxy, 1,1-dimethylethoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, in particular methoxy, ethoxy or 1-methylethoxy; and $C_1$–$C_6$-haloalkoxy, preferably $C_1$–$C_4$-haloalkoxy, in particular $C_1$- or $C_2$-haloalkoxy, such as chloromethoxy, dichloromethoxy, trichloromethoxy, chlorofluoromethoxy, dichlorofluoromethoxy, fluoromethoxy, difluoromethoxy, trifluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, in particular trifluoromethoxy;

$R^2$ is hydrogen;

halogen, such as fluorine, chlorine, bromine or iodine, in particular chlorine or bromine;

$C_1$–$C_8$-alkyl, in particular branched or straight-chain $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular branched or straight-chain $C_1$–$C_4$-alkyl, such as methyl, ethyl, propyl, 1-methylethyl, butyl, 1-methylpropyl, 2-methylpropyl or 1,1-dimethylethyl;

$C_1$–$C_6$-haloalkyl, preferably $C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2,2,2-chloro-2,2-difluoroethyl,2,2-dichloro-2-fluoroethyl, 2,2,2-trichloroethyl and pentafluoroethyl, in particular trifluoromethyl;

$C_1$–$C_6$-alkoxy, such as methoxy, ethoxy, propoxy, 1-methyethoxy, butoxy, 1-methylpropoxy, 2-methylpropoxy, 1,1-dimethylethoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy,1,1,2-trimethylpropoxy,1,2,2-trimethylpropoxy, 1-ethyl-1-methylpropoxy or 1-ethyl-2-methylpropoxy, in particular methoxy, or $C_1$–$C_6$-haloalkoxy, preferably $C_1$–$C_4$-haloalkoxy in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy;

n is 0, 1 or 2, and the radicals may be different when n is 2, and m is 0, 1, 2, 3 or 4, and the radicals may be different when m is 2, 3 or 4.

Particularly preferred 2,2'-thienylbenzothiophenes of the general formula IA are those in which the radicals have the following meanings:

$R^1$ and $R^3$ independently of one another are each halogen, such as fluorine, chlorine, bromine or iodine, in particular chlorine or bromine; branched or straight-chain $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably branched or straight-chain $C_1$–$C_4$-alkyl, such as methyl, ethyl, propyl, 1-methylethyl, butyl, 1-methylpropyl, 2-methylpropyl or 1,1-dimethylethyl;

$C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, or $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy, and $R^2$ is hydrogen;

halogen, such as fluorine, chlorine, bromine or iodine, in particular chlorine or bromine; branched or straight-chain $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, trimethylpropyl, 1,2,2-trimethylpropyl, 1-ethyl-1-methylpropyl and 1-ethyl-2-methylpropyl, in particular branched or straight-chain $C_1$–$C_4$-alkyl, such as methyl, ethyl, propyl, 1-methylethyl, butyl, 1-methylpropyl, 2-methylpropyl or 1,1-dimethylethyl;

$C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, or $C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy;

n is 0, 1 or 2, and the radicals may be different when n is 2, and m is 0, 1, 2 or 3, and the radicals may be different when m is 2 or 3.

Particularly preferred 2,2'-thienylbenzothiophenes of the general formula IA are those in which the radicals have the following meanings:

$R^1$ and $R^3$ independently of one another are each halogen, such as fluorine, chlorine, bromine or iodine, in particular chlorine or bromine;

branched or straight-chain $C_1$–$C_4$-alkyl, such as methyl, ethyl, propyl, 1-methylethyl, butyl, 1-methylpropyl, 2-methylpropyl or 1,1-dimethylethyl;

$C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_1$- or $C_2$-alkoxy, such as methoxy or ethoxy, or $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy;

$R^2$ is hydrogen;

halogen, such as fluorine, chlorine, bromine or iodine, in particular chlorine or bromine;

branched or straight-chain $C_1$–$C_4$-alkyl, such as methyl, ethyl, propyl, 1-methylethyl, butyl, 1-methylpropyl, 2-methylpropyl or 1,1-dimethylethyl;

$C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-1-fluoroethyl,yl, 2,2-dichloro-2-fluoroethyl, 2,2,2-trichloroethyl and pentafluoroethyl;

$C_1$- or $C_2$-alkoxy, such as methoxy or ethoxy, or $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy;

n is 0 or 1 and m is 0, 1 or 2, and the radicals may be different when m is 2.

Examples of particularly preferred compounds of the general formula IA are shown in the Table below.

TABLE

| $(R^1)$ | $R^2$ | $(R^3)_m$ |
|---|---|---|
| — | H | — |
| 5'-Cl | H | — |
| 5'-Br | H | — |
| 5'-CH$_3$ | H | — |
| 5'-Cl | H | 6-CH$_3$O |
| 5'-CH$_3$ | H | 6-CF$_3$ |
| 5'-Cl | H | 5-Cl |
| 5'-CH$_3$ | Cl | 5-Cl |
| 5'-OCH$_3$ | H | 5-Cl |
| 5'-Cl | H | 7-CH$_3$ |
| 4'-CH$_3$ | Cl | 7-CH$_3$ |
| 5'-CH$_2$CH$_3$ | H | 5-CF$_3$ |

TABLE-continued

IA: Structure with benzothiophene-thiophene system, substituents $R^2$, $R^3_m$ (positions 4,5,6,7), $R^1_n$ (positions 3', 4', 5')

| (R¹) | R² | (R³)ₘ |
|---|---|---|
| 5'-Br | Br | — |
| — | Br | — |

The compounds of the formula IA are suitable for effectively controlling pests from the class consisting of the insects, arachnids and nematodes. They can be used as pesticides in crop protection, in the hygiene and veterinary sector and for the protection of stored materials.

The insect pests include, from the order of the butterflies (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* from the order of the beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus* and *Sitophilus granaria;* from the order of the Diptera, for example *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa;* from the order of the Thysanoptera, for example *Frankliniella fusca, Frankliniella occidentalis, Frankliniella tritici, Scirtothrips citri, Thrips oryzae, Thrips palmi* and *Thrips tabaci;* from the order of the Hymenoptera, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta;* from the order of the Heteroptera, for example *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor;* from the order of the Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulocorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum* and *Viteus vitifolii;* from the order of the Isoptera, for example *Calotermes flavicollis, Leucotermes flavipes, Reticulitermes lucifugus* and *Termes natalensis;* from the order of the Orthoptera, for example *Acheta domestica, Blatta orientalis, Blatella germanica, Forficula auricularia, Gryllotalpa gryllotalpa, Locusta migratoria, Melanoplus birittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus;* from the class of the Arachnoidea, for example Acarina, such as *Amblyomma americanum, Amglyomma variegatum, Argas persicus, Boophilus annulatus, Boophilus decolaratus, Boophilus microplus, Brevipalpus phoenicis, Bryobia praetiosa, Dermacentor silvarum, Eotertranychus carpini, Eriophyes sheldoni, Hyalomma trucatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipcephalus appendiculatus, Rhipicephalus evertsi, Saccoptes scabiei, Tetranychus cinnabarinus, Tetranychus kanazawai, Tetranychus pacificus, Tetranychus telarius* and *Tetranychus urticae;* from the class of the nematodes, for example root gall nematodes, eg. *Meloidogyne hapla, Meloidogyne incognita* and *Meloidogyne javanica*, cyst-forming nematodes, eg. *Globodera rostochiensis, Heterodera aveae, Heterodera glycinae, Heterodera schatii, Hetrodera triflolii*, and stem and leaf borers, eg. *Belonalaimus lonicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi*.

The active ingredients can be used as such or in the form of their formulations or of the application forms prepared therefrom, for example in the form of directly sprayable solutions, powders, suspensions or dispersions, emulsions, oil dispersions, pastes, dusting agents, broadcasting agents or granules, by spraying atomizing, dusting, broadcasting or pouring. The application forms depend entirely on the intended uses; they should in any case ensure very fine distribution of the novel active ingredients.

For the preparation of directly sprayable solutions, emulsions, pastes or oil dispersions, mineral oil fractions having a medium to high boiling point, such as kerosene or diesel oil, and coal tar oils and oils of vegetable or animal origin, aliphatic, cyclic and aromatic hydrocarbons, eg. benzene, toluene, xylene or paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone and strongly polar solvents, eg. dimethylformamide, dimethyl sulfoxide, N-methylpyrrolidone or water, are suitable.

Aqueous application forms can be prepared from emulsion concentrates, pastes or wettable powders (spray powders, oil dispersions) by adding water. For the preparation of emulsions, pastes or oil dispersions, the substances, as such or in solution in an oil or solvent, can be homogenized in water by means of wetting agents, adhesives, dispersants or emulsifiers. However, it is also possible to prepare concentrates which consist of active substance, wetting agents, adhesives, dispersants or emulsifiers and possibly solvents or oil and which are suitable for dilution with water.

Suitable surfactants are alkali metal, alkaline earth metal and ammonium salts of ligninsulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and their alkali metal and alkaline earth metal salts, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol ester, ligninsulfite waste liquors and methylcellulose.

Powders, broadcasting agents and dusting agents can be prepared by mixing or milling the active substances together with a solid carrier.

The formulations contain in general from 0.01 to 95, preferably from 0.1 to 90%, by weight of the active ingredient. The active ingredients are used in a purity of from 90 to 100%, preferably from 95 to 100% (according to NMR spectrum).

Examples of formulations are:

I. 5 parts by weight of compound No. 1 are thoroughly mixed with 95 parts by weight of finely divided kaolin. A dusting agent which contains 5% by weight of the active ingredient is obtained in this manner.

II. 30 parts by weight of compound No. 1 are thoroughly mixed with a mixture of 92 parts by weight of silica gel powder and 8 parts by weight of liquid paraffin, which has been sprayed onto the surface of this silica gel. A formulation of the active ingredient having good adhesion and containing 23% by weight of active ingredient is obtained in this manner.

III. 10 parts by weight of compound No. 1 are dissolved in a mixture which consists of 90 parts by weight of xylene, 6 parts by weight of the adduct of from 8 to 10 moles of ethylene oxide with 1 mole of oleic acid N-monoethanolamide, 2 parts by weight of the calcium salt of dodecylbenzenesulfonic acid and 2 parts by weight of the adduct of 40 moles of ethylene oxide with 1 mole of castor oil (active ingredient content 9% by weight).

IV. 20 parts by weight of compound No. 1 are dissolved in a mixture which consists of 60 parts by weight of cyclohexanone, 30 parts by weight of isobutanol, 5 parts by weight of the adduct of 7 moles of ethylene oxide with 1 mole of isooctylphenol and 5 parts by weight of the adduct of 40 moles of ethylene oxide with 1 mole of castor oil (active ingredient content 16% by weight).

V. 80 parts by weight of compound No. 1 are thoroughly mixed with 3 parts by weight of the sodium salt of diisobutylnaphthalene-alphasulfonic acid, 10 parts by weight of the sodium salt of a ligninsulfonic acid obtained from a sulfite waste liquor and 7 parts by weight of silica gel powder, and the mixture is milled in a hammer mill (active ingredient content 80% by weight).

VI. 90 parts by weight of compound No. 1 are mixed with 10 parts by weight of N-methyl-α-pyrrolidone, and a solution which is suitable for use in the form of very small drops is obtained (active ingredient content 90% by weight).

VII. 20 parts by weight of compound No. 1 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

VIII. 20 parts by weight of active ingredient No. 1 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

Granules, for example coated, impregnated and homogeneous granules, can be prepared by binding the active ingredients to solid carriers. Examples of solid carriers are mineral earths, such as silica gel, silicas, silicates, talc, kaolin, attaclay, limestone, lime, chalk, bole, loess, clay, dolomite, kieselguhr, calcium sulfate, magnesium sulfate, magnesium oxide, milled plastics, fertilizers, eg. ammonium sulfate, ammonium phosphate, ammmonium nitrate and ureas, and vegetable products, such as cereal meal, ground bark, woodmeal and nutshell meal, cellulose powder and other solid carriers.

The active ingredient concentrations in the ready-to-use formulations can be varied within wide ranges.

In general, they are from 0.0001 to 10%, preferably from 0.01 to 1%.

The active ingredients can also be successfully used by the ultralow volume method (ULV), and it is possible to apply formulations containing more than 95% by weight of active ingredient or even the active ingredient without additives.

The application rate of active ingredient under open air conditions is from 0.01 to 10, preferably from 0.05 to 5, kg/ha.

Oils of different types, herbicides, fungicides, other pesticides and bactericides may be added to the active ingredients, if necessary immediately before use (tank mix). These agents can be mixed with the novel agents in a weight ratio of from 1:10 to 10:1.

Examples of Syntheses

The method described in the Example of Synthesis below was used to obtain further compounds IA, with appropriate modification of the starting compounds. The compounds thus obtained are shown in the Table below, together with the physical data.

EXAMPLE 1

2,2'-Thienylbenzothiophene

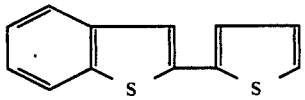

a) 2-Bromobenzothiophene 94.0 g (0.7 mol) of benzothiophene in 940 ml of absolute diethyl ether are initially taken at 20°–30° C., and 332 g (0.77 mol) of a 15% strength solution of n-butyllithium in n-hexane are added dropwise in the course of 2 hours. After one hour, 127 g (0.799 mol) of bromine are added dropwise, also at 0° C., and stirring is continued for 2 hours. After working up was carried out in a conventional manner, 2-bromobenzothiophene is distilled off, finally at 1–1.2 mmHg and 84°–86° C. Yield: 240 g (76%).

b) 2,2'-Thienylbenzothiophene

A Grignard solution of 9.64 g (0.059 mol) of 2-bromothiophene and 1.42 g (0.059 mol) of magnesium in 30 ml of diethyl ether is added dropwise at 25° C. to 10 g (0.047 mol) of 2-bromobenzothiophene and 0.1 g of DPPP-nickel catalyst. Stirring is carried out for 5 hours at 25° C., after which the mixture is worked up in a conventional manner and the product is finally recrystallized from ethyl alcohol containing a little active carbon. Mp. 134°–135° C.; yield 6.8 g (67%).

Use Examples

The insecticidal action of the compounds of the general formula IA were demonstrated by the following experiments:

The active ingredients were prepared
a) as a 0.1% strength solution in acetone or
b) as a 10% strength emulsion in a mixture of 70% by weight of cyclohexanol, 20% by weight of Nekanil ® LN (Lutensol ® AP6, wetting agent having an emulsifying and dispersing action and based on ethoxylated alkylphenols) and 10% by weight of Emulphor ® EL (Emulan ® EL, emulsifier based on ethoxylated fatty alcohols), and diluted to the desired concentration with acetone in the case of a) or with water in the case of b).

After the end of the experiments, the lowest concentration, in each case, at which the compounds still exhibited an 80–100% inhibition or kill rate in comparison with untreated control experiments (activity threshold or minimum concentration (mg)) was determined.

A. *Tetranychus telarius* (red spider), contact action

Heavily infested potted bush beans which had the second pair of secondary leaves were sprayed to run-off with the aqueous active ingredient formulation. After 5 days in a greenhouse, the success of control was determined by means of a binocular microscope. In this test, the compound of Example 1 had an activity threshold of 100 ppm.

B. *Aedes aegypti* (yellow-fever mosquito), breeding experiment

30–40 larvae in the third or fourth larval stage were treated, in 200 ml of water at 23° C., with the aqueous active ingredient formulation. After 24 hours, the kill rate was determined. Thereafter, the experiments were left at 25° C. until the mosquitos in an untreated (control) experiment had hatched, and the inhibition of development was determined in comparison with the untreated control. In this test, the compound of Example 1 had an activity threshold of 0.04 ppm.

We claim:

1. A 2,2'-thienylbenzothiophene of the formula I

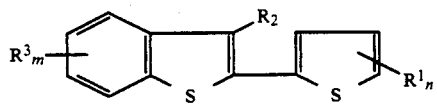

where $R^1$ and $R^3$ independently of one another are each halogen, $C_1$-$C_8$-alkyl, $C_1$-$C_6$-haloalkyl, $C_1$-$C_6$-alkoxy or $C_1$-$C_6$-haloalkoxy, $R^2$ is hydrogen, halogen, $C_1$-$C_8$-alkyl, $C_1$-$C_6$-haloalkyl, $C_1$-$C_6$-alkoxy or $C_1$-$C_6$-haloalkoxy, n is 0, 1 or 2, and the radicals may be different when n is 2, m is 0, 1, 2, 3 or 4, and the radicals may be different when m is 2, 3 or 4, and n and m are not simultaneously 0 when $R^2$ is hydrogen.

2. A 2,2'-thienylbenzothiophene of the formula I as claimed in claim 1, wherein $R^1$ and $R^3$ independently of one another are each halogen, $C_1$-$C_6$-alkyl, $C_1$-$C_4$-haloalkyl, $C_1$-$C_4$-alkoxy or $C_1$-$C_4$-haloalkoxy, $R^2$ is hydrogen halogen $C_1$-$C_6$-alkyl, $C_1$-$C_4$-haloalkyl, $C_1$-$C_4$-alkoxy or $C_1$-$C_4$-haloalkoxy, n is 0, 1 or 2, and the radicals may be different when n is 2, m is 0, 1, 2 or 3, and the radicals may be different when m is 2 or 3, and n and m are not simultaneously 0 when $R^2$ is hydrogen.

3. A 2,2'-thienylbenzothiophene of the formula I as claimed in claim 1, wherein $R^1$ and $R^3$ independently of one another are each halogen, $C_1$-$C_4$-alkyl, $C_1$- or $C_2$-haloalkyl, $C_1$- or $C_2$-alkoxy or $C_1$- or $C_2$-haloalkoxy, $R^2$ is hydrogen, halogen, $C_1$-$C_4$-alkyl, $C_1$- or $C_2$-haloalkyl, $C_1$- or $C_2$-alkoxy or $C_1$- or $C_2$-haloalkoxy, n is 0 or 1, m is 0, 1 or 2, and the radicals may be different when m is 2, and n and m are not simultaneously 0 when $R^2$ is hydrogen.

4. A pesticide containing a compound of the formula I as claimed in claim 1 and inert additives.

5. A method for controlling pests, wherein the pests or their habitat are treated with an effective amount of a compound of the formula IA

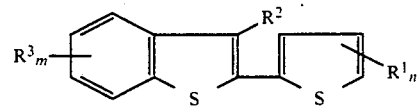

where $R^1$ and $R^3$ independently of one another are each halogen, $C_1$-$C_8$-alkyl, $C_1$-$C_6$-haloalkyl, $C_1$-$C_6$-alkoxy or $C_1$-$C_6$-haloalkoxy, $R^2$ is hydrogen, halogen, $C_1$-$C_8$-alkyl, $C_1$-$C_6$-haloalkyl, $C_1$-$C_6$-alkoxy or $C_1$-$C_6$-haloalkoxy, n is 0, 1 or 2, and the radicals may be different when n is 2 and m is 0, 1, 2, 3 or 4, and the radicals may be different when m is 2, 3 or 4.

* * * * *